United States Patent [19]
Epstein et al.

[11] 4,389,669
[45] Jun. 21, 1983

[54] OPTO-VIDEO INSPECTION SYSTEM

[75] Inventors: Daniel Epstein, Oceanside; Robert Lieberman, Bethpage, both of N.Y.

[73] Assignee: ILC Data Device Corporation, Bohemia, N.Y.

[21] Appl. No.: 238,831

[22] Filed: Feb. 27, 1981

[51] Int. Cl.³ .............................................. H04N 7/18
[52] U.S. Cl. .................................... 358/101; 356/394; 358/106; 358/107; 364/474
[58] Field of Search ................. 358/93, 101, 106, 107; 364/474, 515, 516, 551, 552, 580; 356/388, 392, 393, 394, 398

[56] References Cited

U.S. PATENT DOCUMENTS

| Re. 29,351 | 8/1977 | Zukerman | 358/107 |
|---|---|---|---|
| T. 945,006 | 4/1976 | Speck | 358/107 |
| 3,283,071 | 11/1966 | Rose | 358/93 |
| 3,887,762 | 6/1975 | Uno | 358/101 |
| 3,889,056 | 6/1975 | Mayer | 358/93 |
| 3,986,007 | 10/1976 | Ruoff | 358/101 |
| 3,988,535 | 10/1976 | Hickman | 358/101 |
| 4,028,728 | 6/1977 | Sharp | 358/107 |
| 4,074,350 | 2/1978 | Roch | 364/474 |
| 4,148,065 | 4/1979 | Nakagawa | 358/101 |
| 4,160,263 | 7/1979 | Christy | 358/101 |
| 4,208,675 | 6/1980 | Bajon | 358/101 |
| 4,232,335 | 11/1980 | Nakagawa | 358/101 |
| 4,233,625 | 11/1980 | Altman | 358/101 |
| 4,247,203 | 1/1981 | Levy | 356/398 |
| 4,253,111 | 2/1981 | Funk | 358/101 |
| 4,295,198 | 10/1981 | Copeland | 358/107 |
| 4,301,470 | 11/1981 | Pagany | 358/101 |

Primary Examiner—Howard Britton
Attorney, Agent, or Firm—Weinstein & Sutton

[57] ABSTRACT

An opto-video inspection system for inspecting and examining miniaturized solid-state devices, such as hybrids. An XY table simultaneously positions a known good device and a device to be inspected under respective stereo-zoom microscopes. A TV camera is coupled to each microscope. The XY table, under microprocessor control, is manipulated to select the "target" or wire bond to be viewed. The selected sites may be simultaneously viewed upon a split screen video display or, alternatively, either the known good device or the device being inspected may be separately viewed through the associated stereo-zoom microscope or on the video screen. Dwell time at each site is computer selectable, as is the sequencing of sites to be viewed. Defective bonds, imperfections or other conditions are permanently recorded through a printer which automatically associates the code printed thereby with the site in view at that time. An operator keyboard permits completed program steps to be recalled for review or for reprogramming, if desired. The known good device may be replaced by either a video tape or video disc containing a record of each site to be examined or, alternatively, a strip of photographic film, each site being selected by the microprocessor in accordance with the site of the device under inspection presently being examined.

30 Claims, 11 Drawing Figures

OPTO-VIDEO INSPECTION SYSTEM

FIELD OF THE INVENTION

The present invention relates to inspection systems and more particularly to a novel optical/video inspection system incorporating computer programmed observation means to insure proper and complete inspection of every desired site on the device being examined.

BACKGROUND OF THE INVENTION

With the increasing complexity of solid-state electronic devices such as hybrid microelectronic circuits, which now include large-scale hybrids, it is a practical impossibility to achieve 100% inspection in accordance with established visual inspection criteria, as well as to do a substantive wiring inspection. Visual inspection and reporting are becoming more involved and tedious and require extensive paper reporting and analysis of noted defects and/or imperfections.

The technique presently employed utilizes an XY table which is manually manipulated by the operator to place a circuit under inspection beneath optical viewing apparatus. The minute size of the device under inspection and, more particularly the minute dimensions between and among targets and/wire bonds to be inspected make the movement and observation functions quite tedious and complex, especially since such minute movement requires a high level of manual dexterity which only serves to reduce or degrade the concentration required for the actual inspection. In addition, even minor distractions make it difficult to recall the last target examined prior to the distraction.

BRIEF DESCRIPTION OF THE INVENTION

A solution to the above problems has been developed by providing automated means of performing the required visual inspections. Assistance in inspection is provided to the operator through the employment of stereo-zoom microscopes and TV camera monitors. Preprogrammed microprocessor means selects the target of inspection interest and, since inspection points are not selectable by the operator, distractions have no significant effect and viewing of 100% of the desired inspection points is assured. Missing wires and misdirected wires are virtually eliminated prior to first test.

More specifically, the present invention is characterized by comprising an automated optical video system utilizing a programmable XY table. During one portion of the inspection, comparison of a known good hybrid to the hybrid under inspection is accomplished through the utilization of a split screen video display.

The programmed XY table positions a known good hybrid and a hybrid to be inspected beneath associated ones of the optical/video devices. For those portions of the program during which comparative observations are to be made, the split screen video display displays corresponding portions of the known good hybrid and the hybrid under inspection. The "targets" may be viewed through the stereo-zoom microscope without any concern for the sequence of the program. Dwell time at each target site is preprogrammed in accordance with the nature and complexity of the site being examined. Sequencing of the automated XY table may be temporarily halted to permit a lengthier examination thereof, including movement of the XY table in either a fast or a slow fashion to view the site from a different perspective, as well as providing an enlarged or magnified view of the site under inspection being displayed by the video display device.

Any defects, imperfections or other information worth noting for future reference or rework/repair purposes is accomplished merely by keying in a function code representing the nature of the defect or imperfection or other observation, said code being entered and printed through the medium of a printer keyboard. The printer automatically prints out the sequence number and coordinates of the site under inspection thereby automatically identifying the hybrid and the site on the hybrid which is defective or which requires further consideration.

Any temporary halt in the program, for whatever reason, is totally permissible without altering the program. Return to the program sequence is initiated simply by pressing a start button key. Any previous movement imparted to the XY table for inspection or other purposes has no effect whatsoever upon the XY coordinate stored for each target site.

Upon completion of the inspection of each hybrid the main program automatically steps to the next hybrid to be examined and enters the subroutine which repeats the same sequence for each such hybrid. The known good hybrid is preferably moved to a physical location on the XY table associated with the next hybrid to be examined.

Alternatively, the target sites of the known good hybrid may be stored in a video tape, video disc or in a film strip which is automatically stepped to the target site associated with the target site on the hybrid presently under examination.

The amount of data printed out is kept to a minimum and the programmed operation minimizes operator fatigue and optimizes operator productivity and efficiency.

OBJECTS OF THE INVENTION AND BRIEF DESCRIPTION OF THE FIGURES

It is therefore one object of the present invention to provide a novel automated inspection system for examining and inspecting miniature devices, such as complex microelectronic devices.

Another object of the present invention is to provide a novel inspection system incorporating an automatic preprogrammed XY table for precisely positioning predetermined sites of a miniature device, such as a hybrid, beneath optical observation means.

Still another object of the present invention is to provide a novel inspection system for use in inspecting complex miniaturized devices, such as solid-state circuits and the like and incorporating split screen display means for observing and comparing like sites of a known good device and a similar device under inspection.

Still another object of the present invention is to provide a novel inspection system for complex miniaturized solid-state circuits and the like in which temporary departures from the preprogrammed site examination routine may be undertaken without in any way altering the automated operation.

Still another object of the present invention is to provide a novel inspection system incorporating automated means for inspecting the sites of a complex miniaturized solid-state circuit and including printer means for automatically identifying the circuit under inspection and the site of said circuit associated with a defect code.

The above as well as other objects of the present invention will become apparent when reading the accompanying description and drawing in which:

DETAILED DESCRIPTION OF THE INVENTION AND THE PREFERRED EMBODIMENTS

Figure 1:
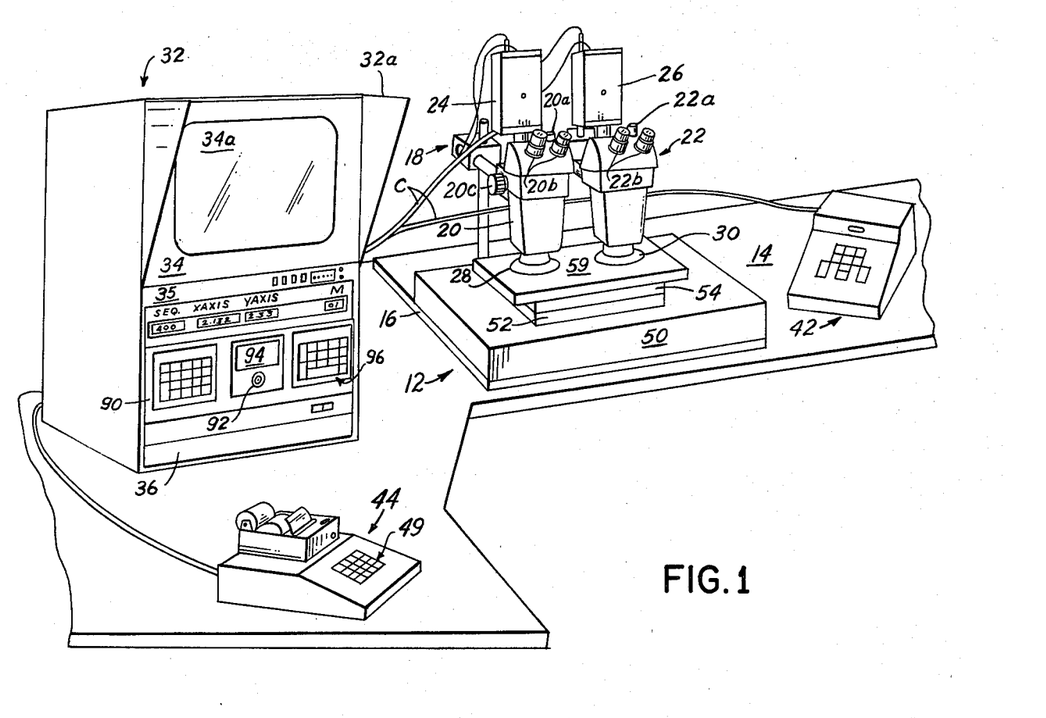
FIG. 1 is a perspective view of an inspection system embodying the principles of the present invention.

FIG. 1 shows an inspection system 10 designed in accordance with the principles of the present invention and comprised of an XY table 12 supported on a surface 14 which in turn supports a base 16 for supporting an adjustment assembly 18 for adjusting the physical positions and orientation of a pair of stereo-zoom microscopes 20 and 22 each having a T.V. camera 24, 26 respectively coupled into one optical path of an associated one of the stereo-zoom microscopes 20 and 22. Annular shaped light sources (ring lights) 28 and 30 illuminate areas on the mounting surface 12A of XY table 12.

A console 32 houses a TV display 34, inserter/splitter 35, digital display 36, programming keyboard 90 and operating keyboard 96. Video display 34 is capable of providing either a single screen view or a split screen view of corresponding areas of a known good hybrid and the hybrid presently under inspection, under control of inserter/splitter 35. Regardless of the subject being viewed, the screen display 34a may be shifted or enlarged at will to facilitate a thorough inspection operation.

A remote keyboard 42 is preferably positioned to the right of support 14 to accommodate either right- or left-handed operators or to facilitate manipulation of the controls normally utilized during an automated inspection operation in the event that the remote keyboard 42 is more accessible than the keyboard 96 provided as part of console 32. A shade 32a on console 32 prevents overhead lighting from creating a glare on the face 34a of the video display.

A printer 44 has a keyboard 49 for printing data representing the particular hybrid and the specific site of the hybrid which has been noted as being defective or having some imperfection. When desired, printer 44 may also print out the entire program sequence.

Figure 4:
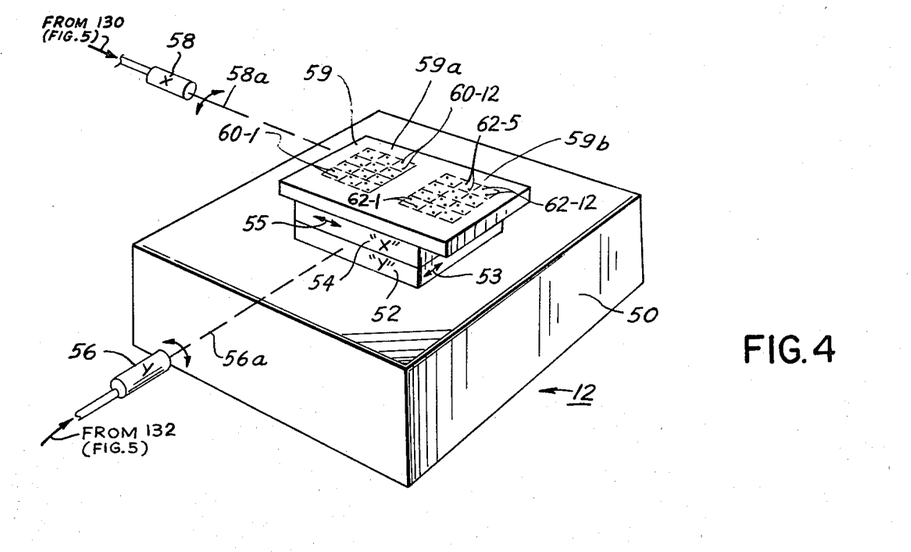
FIG. 4 shows an enlarged perspective view of the XY table employed in the system of FIG. 1.
Figure 4A:
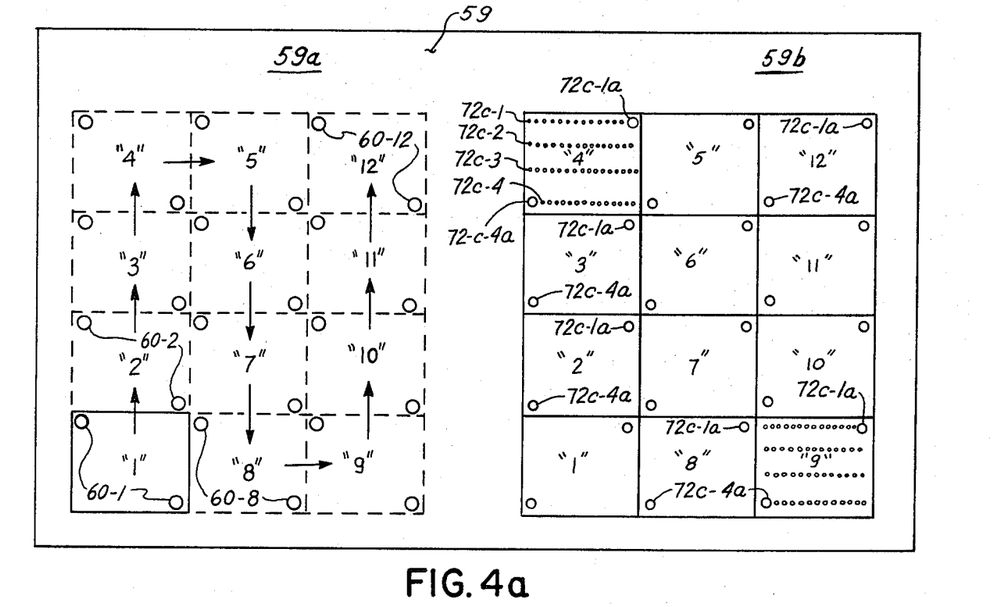
FIG. 4a shows a plan view of the top surface of the XY table of FIG. 4 showing the manner in which circuits under inspection are mounted thereon.

FIGS. 4 and 4a show the XY table 12 comprising housing 50, supporting Y table 52. Reciprocating movement is limited to the "Y" direction, as shown by arrow 53. X table 54 is mounted upon Y table 52 and is reciprocatable but has its movement limited to the "X" direction, as shown by arrow 55. Tooling plate 59 is mounted upon X table 54 and is machined to support hybrid carriers, as will be more fully described hereinbelow. Servo motors 56 and 58 provide mechanical drive to the tables 52 and 54, as represented by the dotted lines 56 and 58a, respectively. For example, servo motors 56 and 58 may be coupled to elongated lead screws (not shown), each having a nut threadedly engaging the lead screw and secured to their associated tables 52, 54 to impart movement thereto. By altering the direction of rotation of the output of servo motors 56 and 58, the direction of movement of the tables 52, 54, is reversed.

The computer 102, as will be described in more detail hereinbelow in connection with FIG. 5, manipulates the XY table 12 in a preprogrammed sequence. For example, by providing digital code words which may be converted to analog signals for imparting drive to the associated servo motors 56 and 58. Alternatively, stepping motors may be provided, each stepping their associated table by a constant increment such as 0.001 inch.

The tooling plate 59 is arranged relative to the stereo-zoom microscopes 20 and 22 (see FIG. 1) so that its left-hand half 59a is arranged beneath binocular microscope 20, and supports a known good hybrid for examination by microscope 20. The right-hand half 59b of tooling plate 59 is arranged generally beneath binocular microscope 22 and positions and supports the hybrids to be inspected. The left-hand half 59a of tooling plate 59 is provided with a plurality of pairs of openings 60-1 through 60-12, arranged to receive a hybrid carrier of the type shown by carrier 70 of FIG. 7. The right-hand half 59b of tooling plate 59 is similarly provided with pairs of openings 62-1 through 62-12 for receiving and supporting a carrier 72. The pairs of openings 60 and 62 generally have the same inner diameters and the pins to be received therein have the same outer diameters to conform with the inner diameters of the openings in which they are intended to be inserted. The sets of openings 60 and 62 are accurately positioned and aligned relative to one another to facilitate the inspection operation. For example, when the X and Y tables 52 and 54 are moved to position the carrier location openings 72c-1a of a carrier 70 having the known good hybrid beneath stereo-zoom microscope 20, the opening 62-1a of the carrier 70 mounted at position "1" of tooling plate position 59b is automatically positioned beneath stereo-zoom microscope 22, the details of the operation being described fully hereinbelow.

Figure 7:
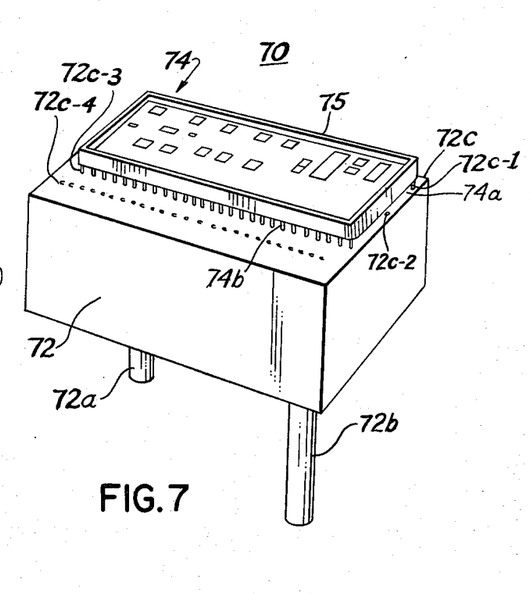
FIG. 7 shows a perspective view of a hybrid carrier having a typical hybrid circuit mounted thereon.

A typical hybrid carrier 70 for supporting a hybrid circuit 74 to be examined is shown in FIG. 7 and is comprised of a solid block 72, having a pair of pins 72a and 72b, integral with, and extending downwardly from, the bottom of block 72. The top surface 72c has a plurality of arrays of small openings 72c-1 through 72c-4, the openings in each array preferably being arranged in a uniformly spaced manner and the arrays 72c-1 through 72c-4 being spaced from one another to receive the pins of the pin arrays 74a and 74b provided along opposite parallel edges of hybrid circuit 74. Providing a plurality of arrays of openings 72c-1 through 72c-4 enables hybrids of varying length and width to be mounted thereon.

The carrier 70 may be placed in any one of the locations having a pair of pins 62-1 through 62-12 arranged on the right-hand half 59a of tooling plate 59. Each carrier block 70 (see FIG. 7) occupies a numbered location and remains fixed on the right-hand side 59b of tooling plate 59.

A detailed view of the hybrid carrier for mounting a known good hybrid has been omitted for purposes of simplicity and is substantially the same as the carrier 70 shown in FIG. 7. The pin hole arrays and block size of the carrier 70 are also identical for both the carrier 70 shown in FIG. 7 and the carrier provided for mounting a known good hybrid. Obviously, when mounting hybrids of either the known good type or of the type to be inspected, all of such hybrids should be mounted utilizing the same pin hole arrays 72c-1 through 72c-4 and the same pin holes within said arrays in order to assure that the identical target sites of the hybrid under inspection and the known good hybrid are beneath and in focus under their respective stereo-zoom microscopes 20 and 22.

Figure 6:
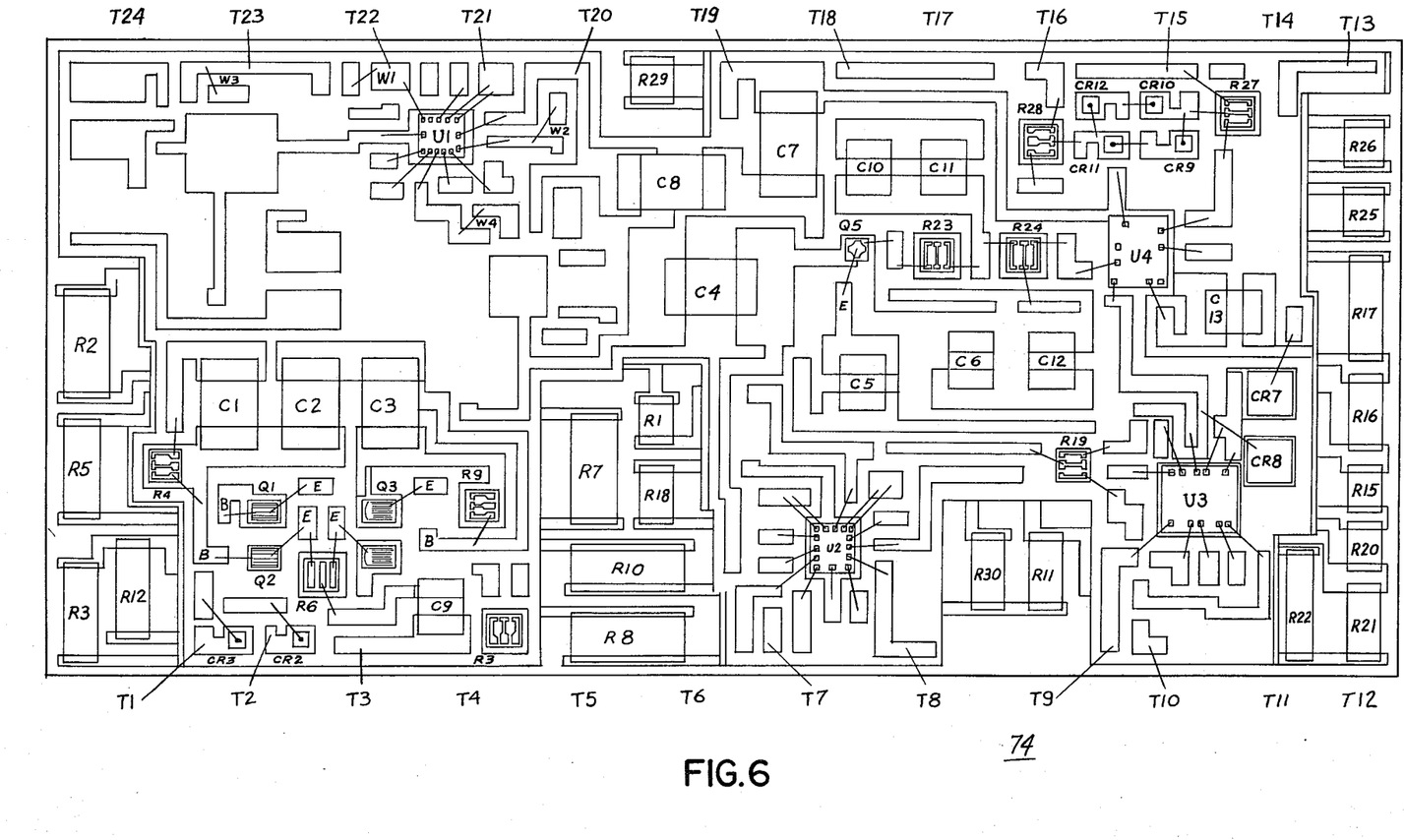
FIG. 6 shows a plan view of a typical hybrid which may be inspected through the use of the system of FIG. 1.

A typical hybrid such as for example the hybrid 74, which may be examined through the use of the inspection 10 of the present invention, is shown in perspective in FIG. 7 and is shown in greater detail in FIG. 6. The size of the hybrid shown in FIG. 6 has been greatly enlarged to facilitate an understanding thereof. However, it should be understood that the actual length of the hybrid shown in FIG. 6 is 1.24" while the width is 0.56". The solid state devices mounted thereon can be seen to be quite small. For example, the semiconductor device identified by the designation U3, which incorporates a plurality of solid state elements such as transistors, diodes and the like, has a length of 0.076" and a width of 0.06". The components designated with the letter U, i.e. U1 through U4 are integrated circuits containing a plurality of components such as transistors, diodes, etc. The elements R1 through R31 are resistance elements; Q1 through Q5 are individual transistor elements; C1 through C12 are capacitors; CR1 through CR12 are diodes; W are wire connections and T1 through T24 are terminals which are in turn connected to the pins of pin arrays 74a and 74b described hereinabove. The circuit board is mounted in a base 75 which mechanically supports pin arrays 74a and 74b.

The semiconductor devices U1 through U4, as well as some of the other elements forming an integral part of the hybrid circuit 74, are interconnected with other circuit elements by means of wire leads, typically gold leads, of one mil thickness. The type of bonding operations may vary depending upon the nature of the components involved. In the examplary hybrid 74 there are 104 wire bonds; 26 die bonds and 12 cap bonds. In addition to inspecting each of the 142 bonds for both their electrical and mechanical integrity, it is important to examine each of the capacitor, resistor and semiconductor devices to be assured of their quality and integrity, at least from the point of view of visual inspection. As will be described in detail hereinbelow, the automated XY table 12 sequentially advances through a series of the order of 90 steps in order to inspect all of the wire bonds and components mentioned hereinabove. Many of the target sites brought into view by the XY table 12 encompass two or more wire bonds and/or components, thereby reducing the total number of steps to a lesser number than the total number of components and wire bonds. As will be described in more detail hereinbelow, it is nevertheless possible to further enlarge a target site being examined to provide a closer, enlarged view of a smaller portion of a target site, if desired. Also, the magnification of the microscope 22, for example, may be reduced to enlarge the field of view.

Figure 3:
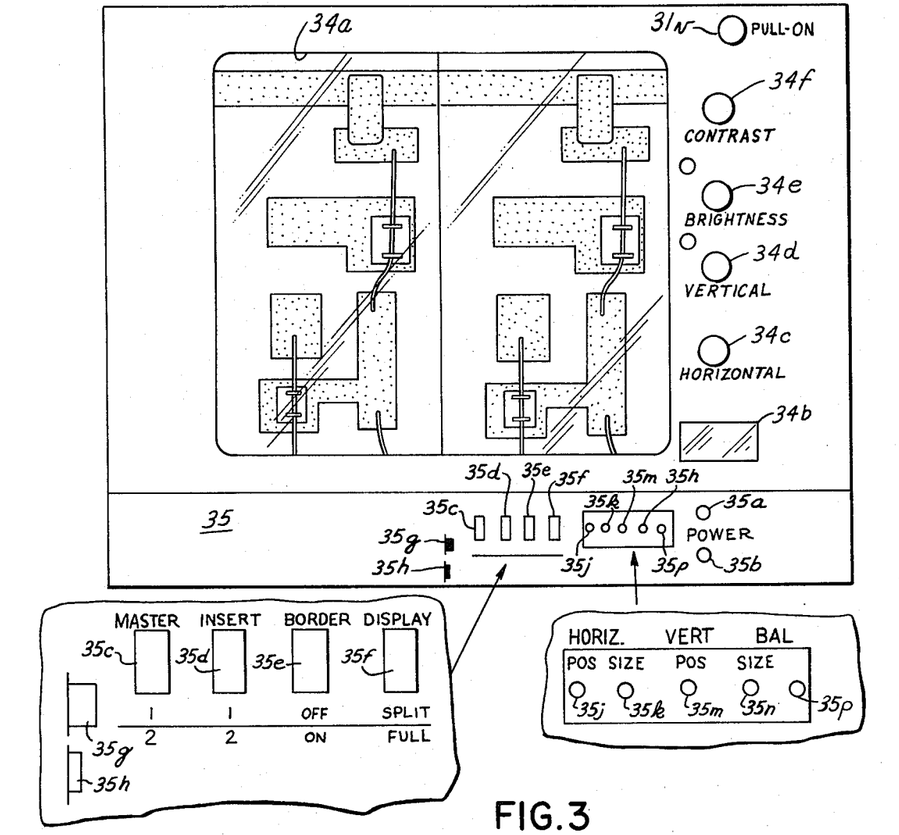
FIG. 3 shows a detailed view of the video display incorporated in the system of FIG. 1 and showing a typical split screen view capable of being displayed thereon.

As was mentioned hereinabove, corresponding portions of the known good hybrid and the hybrid under inspection may be simultaneously observed through the split screen video display 34, shown in FIG. 1 and shown in further detail in FIG. 3. The display screen 34a shows corresponding portions 74' and 74" of a known good hybrid and a hybrid under inspection to permit inspection and comparison therebetween, enabling the operator to observe any differences as between the known good hybrid and the hybrid under inspection, which differences may vary well be defects. The operating controls of video display 34 include a lamp indicator 34b which is illuminated when the system pull-on switch 34v is pulled out; and horizontal, vertical, brightness and contrast controls 34c through 34f, respectively, for making appropriate adjustments, as is conventional in video displays.

Power switch button 35a, when depressed the first time, turns the inserter/splitter unit 35 on and, when depressed a second time, turns it off. A lamp (not shown) behind colored lens 35b is illuminated to indicate that the inserter/splitter unit 35 is turned on and vice versa. The array of buttons 35c through 35f have two settable positions as shown in the inset. When the buttons are depressed and are in the "in" position, shown at 35g, they are automatically reset to the "out" position shown at 35h. When any of the buttons 35c–35f occupy position 35g and are depressed, they are set to the "in" position 35h. When display button 35f is in the outer (SPLIT) position, a split screen viewing condition is provided. When button 35f is in the "in" position a full screen presentation will be displayed at 34a. The known good hybrid may be displayed on the full screen by placing button 35c in the "out" position as shown at 35g. When the split screen mode is selected, the known good hybrid will be positioned in the left-hand half of the split screen when button 35c is in the "out" position and will be positioned in the right-hand half of the split screen when button 35c is in the "in" position. In a similar fashion, the hybrid under inspection will be on display when the full screen mode is selected by button 35f, when 35d is in the "out" position. When the split screen mode is selected by button 35f, the hybrid under inspection will be in the left-hand half of the screen when button 35d is in the "out" position and conversely will be in the right-hand half of the split screen when button 35d is in the "in" position.

The border button 35e, when in the "off" condition (i.e., "out" position), removes the border between the split screen images. When in the "on" condition (i.e. "in" position) the border is reinserted.

Screwdriver adjustment controls 35j through 35n provide size and position adjustments for both the split and full screen displays. For example, controls 35j and 35k enable the position and size of the target site being displayed to be adjusted in the horizontal direction. Controls 35m and 35n provide the same capability in the vertical direction. Control 35p provides a contrast balancing capability for both sides of the split screen.

The stereo-zoom microscopes 20 and 22, may, for example, be Bausch and Lomb microscopes, and have mounted in at least one of their optical paths the TV cameras 24 and 26 which are electrically connected to the video display 34 through a suitable cable C. Depending upon the sequence of the program, the TV cameras 24, 26 may be either switched into or out of operation by means of a control knob such as for example the control knob 78 movable between the "in" and "out" positions 78a and 78b (see FIG. 1a) to respectively couple the TV camera 26 with the video display 34 or to decouple the TV camera 26 from the video display 34.

Figures 2, 2A:
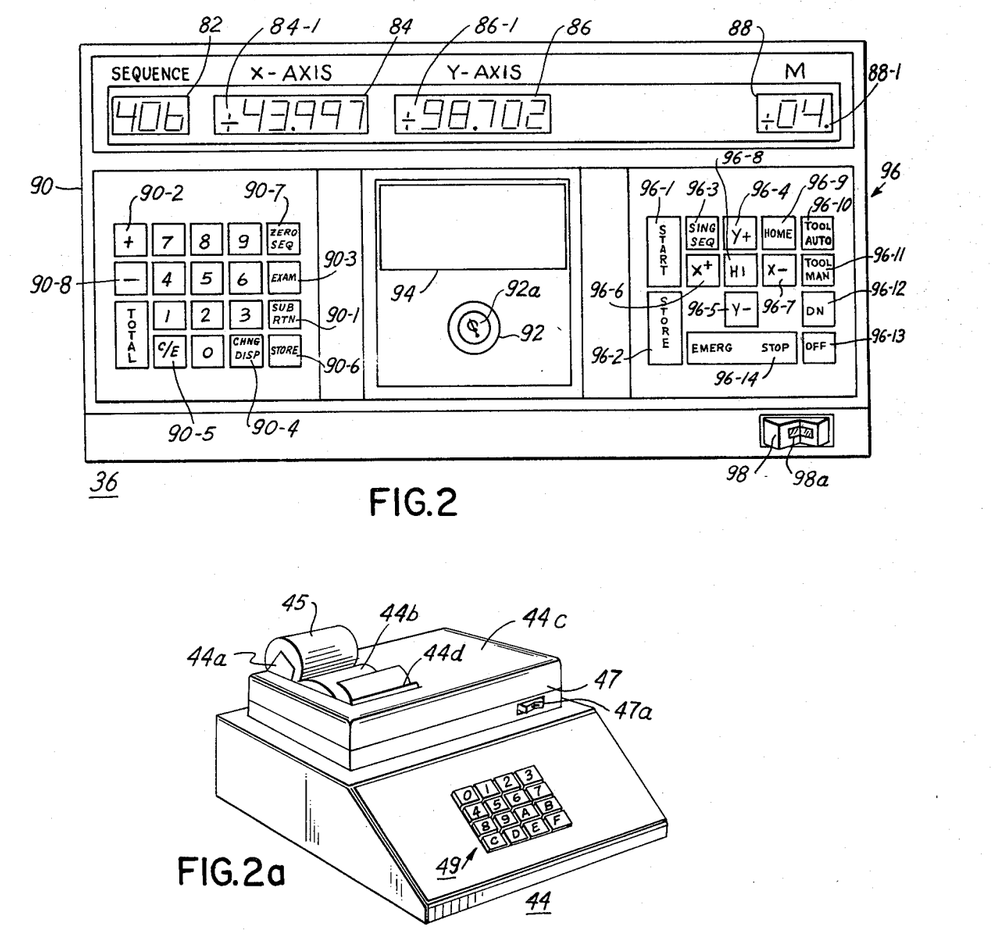
FIG. 2 shows a detailed plan view of the main keyboard and display of FIG. 1.
FIG. 2a shows a detailed perspective view of the printer employed in the system of FIG. 1.

The digital displays 82–88 and programming and manual keyboard arrays 90 and 96, shown in FIG. 1, are also shown in further detail in FIG. 2 and comprise four discrete digital displays 82, 84, 86, and 88 respectively displaying the present sequence step (SEQUENCE), the deviation distance measured in the X axis to which the X table has advanced relative to a home or start position (X AXIS); the displacement distance that the X table has moved relative to the home position measured in the Y direction (Y AXIS); and the mode display (M).

The left-hand keyboard 90 is comprised of an array of keys for use in either initially programming the computer 102, altering existing program steps or jumping either forward or backward and out of sequence and directly to another program step for either inspection or programming purposes as will be described in greater detail hereinbelow.

Switch 92, which is key operated, requires the presence of a key (not shown) into the lock portion 92a to enable the switch to be moved to either the LOAD or the RUN position. In the LOAD position, the computer program may be entered or jumps may be made to particular program steps without going through the normal operating sequence. In the run position, the program has been completely entered and the inspection routine under control of the program may be initiated and inspection may take place without in any way affecting or altering the stored program.

The swingable door 94 may be lifted to expose an interior cavity forming part of a magnetic tape reading device 114 (not shown in FIG. 2 for purposes of simplicity) which is utilized to enter a program stored in the tape of a conventional magnetic tape cassette. The manner in which a pretaped program may be entered will be described hereinbelow.

The right-hand keyboard 96 comprises an array of keys utilized during the inspection routine. START button 96-1 permits the program to be restarted after a halt. By depressing STOP button 96-2, the program will temporarily halt at its present location. Depressing SING SEQ, (i.e. single sequence) button 96-3, the program may be advanced from one program step to the next each time button 96-3 is depressed. Operation of button 96-3, however, does not supercede programmed dwell time for each sequence of the inspection cycle.

The Y+ button 96-4, the Y− button 96-5, the X+ button 96-6 and the X− button 96-7, when selectively depressed, step XY table 12 through an increment of the order of 0.001" in either the ±X or the ±Y direction. If it is desired to step XY table 12 through a distance greater than the 0.001" increment, the HI (high speed) button 96-8 is depressed simultaneously with one of the buttons 96-4 through 96-7 causing XY table 12 to be stepped through a successive number of 0.001" increments at a rapid rate.

HOME button 96-9 causes XY table 12 to be reset to the zero or home location and further resets the sequence and axis display 82, 84 and 86 to zero.

The TOOL AUTO (programmed dwell time) button 96-10 has two operating states and operates a pilot light, in the form of a decimal point 88-1, forming part of display 88. When the decimal point 88-1 is "on", the inspection sequence is stepped through in the preprogrammed manner, including the dwell times allotted for each inspection site. When button 96-10 is pressed a second time, causing the decimal point 88-1 to turn "off", the computer will advance through the program steps rapidly and will ignore all dwell times and any other functions.

The TOOL MAN (i.e., system manual) pushbutton 96-11 allows the operator to exert manual control over the machine functions, as will be more fully described.

ON button 96-12 activates the total system, while OFF button 96-13 turns off the complete system except for the memory. Emergency STOP button 96-14 also turns off the complete system except for the memory.

Main power switch 98, which is provided with an illuminated "power on" indicator 98a controls power to the entire system.

Figure 2B:
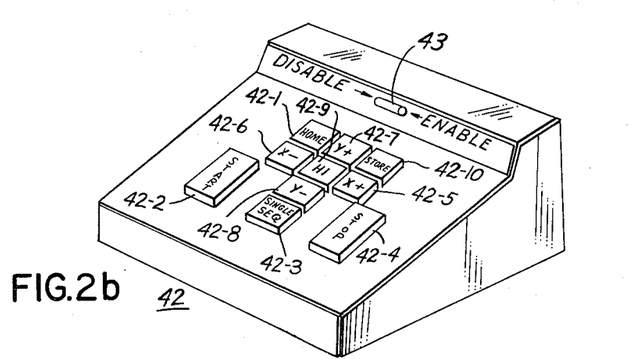
FIG. 2b shows a detailed perspective view of the remote control keyboard employed in the system of FIG. 1.

The remote control keyboard 42 shown in greater detail in FIG. 2b, has a keyboard array which is substantially similar to that of the keyboard array 96 shown in FIG. 2, and is comprised of a HOME key 42-1 performing the same function as HOME key 96-9. START key 42-2 performs the same function as START key 96-1. SING SEQ key 42-3 performs the same operation as SING SEQ key 96-3. STOP button 42-4 performs the same function as STOP button 96-2. The + and −, X and Y jog buttons 42-5 through 42-8 perform the same functions as buttons 96-4 through 96-7 respectively and HI button 42-9 performs the same function as HI button 96-8.

Toggle switch 43, which has a DISABLE and an ENABLE position, must be in the DISABLE position when using keyboard 42 for inspection purposes to prevent any alteration of the program. When in the ENABLE position, remote storage of data is permitted for programming purposes. In order to store data, toggle switch 43 is moved to the ENABLE position and STORE button 42-10 is pressed, causing data shown in the display windows 82, 84, 86 and 88 to be stored, as will be more fully described hereinbelow.

The printer 44 shown in FIG. 1 and shown in greater detail in FIG. 2a is comprised of a paper supply mount 44a for supporting a roll of paper tape 45. The paper is fed through the machine and between a platen 44b and printing mechanism (not shown) mounted within housing 44c. A combination tear bar/window 44d permits inspection of the last line printed as well as facilitating the tearing of a strip of paper web from the main body thereof. Switch 47 selectively turns the printer 44 on and off and is provided with a "power on" indicator 47a which indicates that the printer is "on" when illuminated.

Keyboard 49 is comprised of a 4×4 array of keys representing the decimal digits "0" through "9" and the alphabetic symbols "A" through "F" for a total of 16 different keys.

The operation of printer 44 is such that when a defect or other imperfection is noted, a 2 character code is entered, which code represents the nature of the defect.

Printer 44 initially prints the selected code and thereafter, under control of microprocessor 102, automatically prints out the information displayed by digital displays 82 through 88 (see FIG. 2), thus assuring that the particular defect or imperfection which has been noted is automatically associated with the correct target site.

Figure 5:
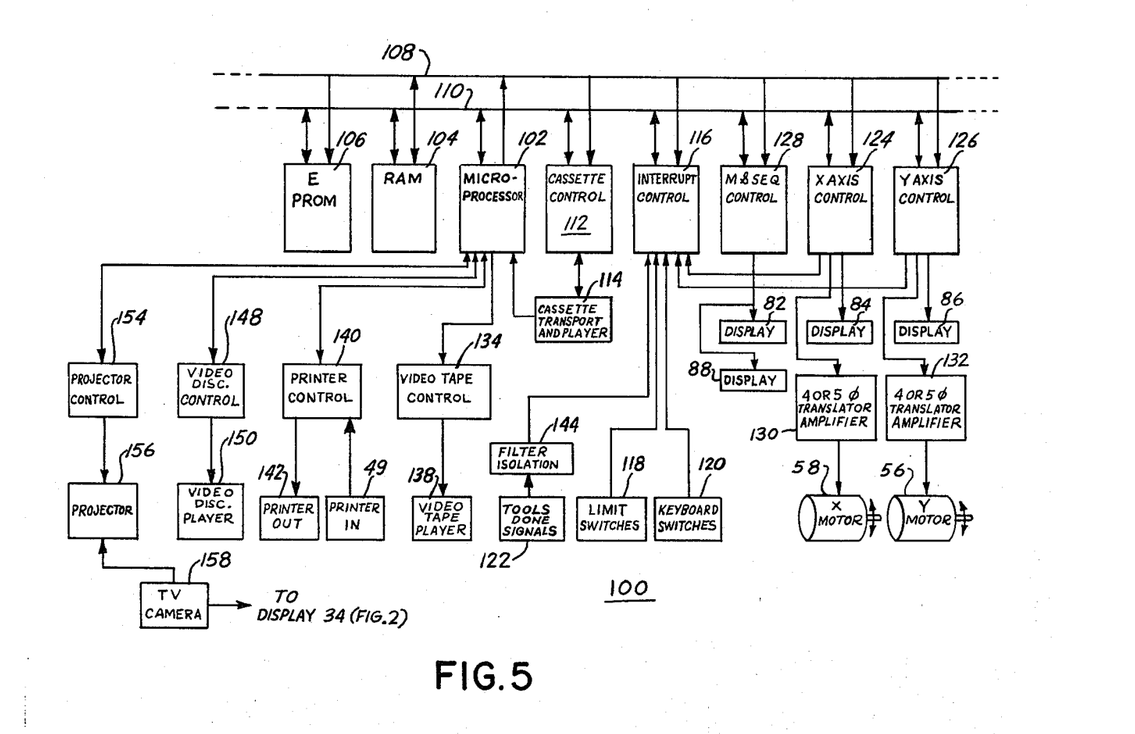
FIG. 5 shows a block diagram of the control electronics for the system of FIG. 1 and showing the computer employed therein.

FIG. 5 shows a block diagram of the electronic control circuitry 100 employed in the present invention comprised of microprocessor 102 which may, for example, be any conventional microprocessor such as, for example, the SC/MP microprocessor produced by National Semiconductor Corp. and which is an eight bit microprocessor. A random access memory (RAM) 104 and an erasable programmable read-only memory (EPROM) 106 are connected to microprocessor 102 through 16 bit address bus 108 and 8 bit data and command bus 110.

A cassette control 112 is similarly connected to address bus 108 and data bus 110 and operates cassette transport and player 114 under control of the microprocessor 102 for purposes of manipulating the tape and either reading data from the magnetic tape or writing data on the magnetic tape.

Interrupt control circuit 116 is coupled to microprocessor 102 through the address and data busses 108 and 110 and, responsive to limit switch 118, keyboard switches represented as numeral 120 in FIG. 5, tools done signals 122 and X axis and Y axis control devices 124 and 126, interrupts the program presently in process in order to cause the microprocessor 102 to attend to a matter of greater priority.

The M and sequence control circuit 128, coupled to address bus 108 and data bus 110, operates under the control of microprocessor 102 to control the data displayed in displays 82 and 88 (note also FIG. 2).

X axis control circuit 124 and Y axis control circuit 126 are respectively coupled to address bus 108 and data bus 110 and further interface with interrupt control circuit 116 to provide an interrupt state under certain operating conditions. X and Y axis control circuits 1124 and 126 are further coupled to control the data displayed by displays 84 and 86 and also to provide operating signals to translator amplifiers 130 and 132 respectively which operate the X and Y motors 58 and 56 (not also FIG. 4). In the preferred embodiment, RAM 104 has a capacity for storing 4,000, 8-bit words while the EPROM has the capacity for storing 8,000 words. The programs are stored in EPROM 106.

The printer input, in the form of keyboard array 49 is coupled to microprocessor 102 through printer control interface 140. The signals utilized to control printing are coupled from the microprocessor 102 through printer control 140 and to the printing device through printer output 142.

The operation of the inspection is as follows:

As was mentioned hereinabove, the program has preferably been previously created and stored in a suitable conventional magnetic tape cassette. The program is inserted into the computer by depressing HOME button 96-9. The symbols in the form of colons 84-1 and 86-1 in the X and Y displays 84 and 86 respectively, are illuminated to indicate that the XY table 12 is not in the home position. When the XY table 12 has reached the home position, the colon symbols 84-1 and 86-1 disappear. At this time, the tape load door 94 is lifted and the tape cartridge is inserted into the reader. The LOAD/RUN key switch 92 is switched to the LOAD position, and the SUBROUTINE and + buttons 90-1 and 90-2 are pressed. At this time any zeros in the sequence display window 82 disappear indicating that the program is now in the process of loading. When zeros (000) reappear in the sequence display 82, this indicates that the program has been completely loaded into memory 106. In the event that an error has occurred, all E's will appear in each display position of the display 84 indicating an error and further indicating that the microprocessor 102 has not accepted the program.

Now that the program has been loaded, an inspection procedure may be initiated and is as follows.

Initially the LOAD/RUN key 92 is switched to the RUN position and HOME button 96-9 is pressed (see FIG. 2).

In order to be assured that all dwell times incorporated into the program are activated, button 96-10 is pressed causing decimal point 88-1 to be illuminated, thereby assuring that all dwell times written into the program will be observed.

A known good hybrid is mounted upon a carrier similar to carrier 70 and is placed upon the left-hand half 59a of tooling plate 59 so that its pins are received in the first pair of openings 60-1. A number of carriers 70 up to the maximum of 12 may each be fitted to receive a hybrid 74 to be examined and the carriers 70 are mounted so that their pins 72a and 72b are received within the associated pairs of openings 62-1 through 62-12. Carriers 70 are preferably fixed in place on the right-hand half 59b of tooling plate 59. Hybrids, such as hybrid 74, are fitted into carriers 70. Although the preferred embodiment described herein shows the capability of loading 12 hybrids for inspection, it should be understood that the system may be modified to accept a lesser or greater number of hybrids for inspection. Also, other devices may be inspected, if desired.

Figure 1A:
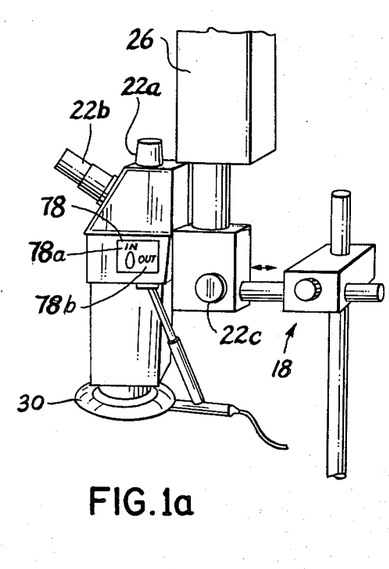
FIG. 1a is a side view of one combination of stereo-zoom microscope/T.V. camera and the selective switch means therefor.

In accordance with a written inspection sheet, setting forth all of the program steps to be performed by the stored program, the operator determines therefrom as to whether the microscopes 20, 22 or the video display 34 is to be utilized. In the event the video screen 34a is indicated for part of the program, the IN/OUT control knobs such as, for example, the control knob 78 are moved to the position which selectively either removes or includes the TV cameras 24, 26 in the operative circuit in accordance with the requirement of the phase of the program to be performed.

The magnification control knobs 20a and 22a of stereo-zoom microscopes 20 and 22 are set in accordance with the printed program sheet.

The SING SEQ button 96-3 is pressed, causing the program to step from the main program routine to the 000 sequence of the subroutine. At this time, the magnification of the binocular microscope 22 is set at 1× and the cross-hairs within the microscope 22 are viewed to be sure that their intersection is in alignment with the center of the top right-hand hole 60-1 of the hybrid carrier 70 mounted thereon. Adjustment of the positioning of microscope 22 may be performed as needed. The inspection system 10 is now ready for initiating automated operation of the XY table and such automated operation begins by pressing START button 96-1. Some typical program steps for example for examining the hybrid 74 shown in FIGS. 6 and 7 will now be described:

The microprocessor 102 causes the program step of the main program to be selected. Step 1 of the main program operates the XY table 12 to place the known good hybrid and the hybrid under inspection in the left and right-hand "1" position to be placed beneath their respective stereo-zoom microscopes 20 and 22. Thereafter, the program jumps from the main routine to the subroutine for inspection of the hybrids in the left and right-hand "1" positions. As was mentioned hereinabove, the first program step of the subroutine. i.e. step 000, enables the operator to check the alignments of the microscope cross hairs of microscope 22 with the upper right-hand-most opening in carrier 70. Since this has already been accomplished, the observation and adjustment step need not be repeated and the system will then step to program step 001 after a preprogrammed dwell time which, in the preferred embodiment, is either 3 seconds or an integral multiple thereof.

During program step 001, the magnification of both microscopes 20 and 22 is set to 1.4×. In the event that the dwell time for the first program time is insufficient to make the adjustment, STOP buttom 96-2 may be pressed to terminate the program for a period of time sufficient to allow adjustment of the magnification knobs 20a, 22a. Thereafter, the START button 96-1 is pressed. During program step 001, the lower left portion of both the known good hybrid and the hybrid under inspection will be respectively positioned beneath their associated binocular microscopes 20 and 22. TV cameras 24 and 26 are turned on to view the respective portions of the hybrids, in this case the lower left portion, from one optical path of their associated stereo-zoom microscopes 20 and 22 and display these portions, preferably upon the left and right-hand halves of the video display screen 34a. The XY table 12 will have moved to a position displaced a predetermined distance in the X and Y directions from the HOME position. In this particular example, the X and Y distances are 1.598" and 0.785", respectively. The left-hand digit of the number displayed by display 88 (FIG. 2) represents the subroutine or "canned" program identification number. The right-hand digit of display 88 represents program commands such as dwell time, automatic stop, return to home, end program and so forth. For example, decimal digit "9" represents "return to home"; "7" represents a dwell time of 3 seconds; "8" represents a dwell time of 6 seconds; and "2" indicates an end of program.

During program step (SEQUENCE) 001, displayed at 82, the lower left portions of the known good hybrid and the hybrid under inspection are checked and compared, one against the other. In the event that no defects are observed, the operator need not perform any active step at this time since the program will advance to step 002 after the aforementioned dwell time incorporated into the program.

Stepping to (sequence) 002, the XY table 12 moves to place the lower middle portions of the known good hybrid and the hybrid under inspections beneath their respective stereo-zoom microscopes 20, 22. The X and Y readings at these times are 1.111 and 0.785 respectively and the dwell time is 6 seconds. As was mentioned hereinabove, in the event that no defects or imperfections are noted or in the event that there are no deviations in the orientation of the components of the known good hybrid as compared with the hybrid under inspection, no action need be taken by the operator. In the event that a defect or other imperfection is noted, the operator simply presses STOP button 96-2 to temporarily halt the program at program step 002 (for example) and enters a two digit code representing the particular defect or imperfection which has been observed by operating the keyboard 49 of printer 44. This two bit code is printed and simultaneously therewith the display information presently being displayed by X axis, Y axis and M displays 84, 86 and 88 are simultaneously printed by the printer 44. The operator may also remain for a longer period of time on the same hybrid beneath stereo-zoom microscope 20 in order to make a comparative evaluation. The operator may alter the magnification of the stereo-zoom microscope depending only upon the needs of the operator. In the event that a portion of the target site at or near the perimeter thereof or slightly beyond the perimeter thereof appears to be of concern in that it may have a defect or imperfection, or for any other reason, the operator may "jog" the XY table 12 by either small increments in either the +X or -X direction or the +Y or -Y direction in order to bring the desired area into the central region of the field of view of the stereo-zoom microscope 20 or 22 presently being viewed by the operator. Since the system is in the RUN mode, jogging of the XY table 12 does not in any way alter the stored location of any of the program steps and the XY table 12 will automatically be stepped to the next site called for by the next program step, regardless of how great or how small a displacement has been imparted to the XY table 12 relative to the position occupied by the XY table during the last program step. The operator may remain at the aforesaid target site or at a displacement distance therefrom for a period sufficient to satisfy the operator as to the nature of the condition observed at which time the operator may either enter a defect code into printer 44 or alternatively may return to the program by pressing START button 96-1 without making any entry into the printer keyboard 49.

As was mentioned hereinabove, either keyboard 96 or remote control keyboard 44 may be utilized to start and stop the program and to jog the XY table in either 0.001" increments or in a sequence of such increments, when depressing the HI button 42-8, for example. Preferably, the console 32 is positioned to one side, for example the left-hand side of the XY table 12 while the remote control keyboard 42 is positioned to the right-hand side of XY table 12, allowing the operator the option of selecting either one of the keyboards 96 or 44 all of the time or alternating as between the two keyboards 96 and 44 if it suits the needs and efficiency of the operator.

In addition to providing the capability of temporarily halting the program by pressing either STOP button 96-1 (See FIG. 2) or 42-4 (See FIG. 2b) automatic stops have been incorporated into the initial sequence of each section of the program. Whenever the digital representation "06" or "16" appears in display 88, at such time, the preprogrammed sequence automatically stops to allow the operator time to make necessary adjustments in microscope, TV camera selection, magnification and so forth.

In order to resume the program, the operator need simply press the START button 96-1 (or 42-2).

Another option for the operator is the use of the SING SEQ (single sequence) button which advances the program only one step at a time allowing the operator additional time for proper inspection at each program step. This technique is beneficial, for example, to less experienced operators.

In the event that it is desired to return to a particular program step, this is accomplished by pressing HOME button 96-9 (See FIG. 2). The switch lock 92 is then moved to the LOAD position. The EXAM (examine) button 90-3 is then pressed causing the program steps to advance rapidly until the operator arrives at the desired sequence of the main program.

At this time, switch 92 is switched to the RUN position. SING SEQ button 96-3 is pressed to move the XY table 12 to the desired carrier 72. Thereafter, SING SEQ button 96-3 is depressed again to advance from the main program to the first step of the subroutine at which time display 88 displays the decimal code "10". The switch key 92 is then switched to the load position and the EXAMINE key 90-3 is again set to examine the program steps as the microprocessor 102 rapidly steps through the sequence of the subroutine. Thereafter, switch 92 is reset to the RUN position and SING SEQ button 96-3 is pressed causing the XY table 12 to move to the selected location.

In order to advance to a particular sequence within the subroutine during which time the subroutine is already being performed, the selection process requires only that the switch 92 be set to the LOAD position, and that EXAM button 90-3 is pressed to examine the program until the desired sequence is displayed in display 82, at which time switch 92 is reset to the RUN position and SING SEQ button 96-3 is pressed to move the XY table 12 to the selected location.

In addition to entering the program from a magnetic tape cassette, two alternative methods may be utilized to both create and load the program, which methods may be used either independently of one another or in combination.

The first one of said methods, identified as the direct programming method, is performed by directly entering data into system 10 using the digit keys of the load keyboard array 90 shown in FIG. 2. The other of said methods, referred to as the digitizing programming method, is accomplished through the use of the jogging buttons 96-4 through 96-7 for "walking" the XY table 12 around under the stereo-zoom microscopes 20 and 22. The location (i.e. displacement) of tooling plate 59 is displayed at all times in displays 84 and 86 and the data displayed therein may be entered into memory by use of the STORE button 90-4 of keyboard array 90 (shown in FIG. 2) or the STORE button 42-10 of remote control keyboard 42 (shown in FIG. 2B) and when switch 43 is in the ENABLE position.

Total communication between the operator and the system 10 during both programming and inspection is accomplished through displays 82, 84, 86 and 88 which are utilized to display the data as it is being entered, to display the data to be stored for examination prior to entry and to indicate the progress of the program being developed and the location of the XY table 12 when a program is being executed.

The displays have a brilliant feature such that, when LOAD/RUN key switch 92 is moved to the LOAD position, one of the displays 84, 86 or 88 will be brilliant compared to the others, signifying to the operator which display is in direct communication with the LOAD keyboard array 90. To select one of the displays for data input or to alter the display from that which is presently in the brilliant state, the CHNG DISP (change display) key 90-4 is pressed. Each time button 90-4 is depressed, the brilliant feature moves to the right from display 84 one display at a time until the brilliant condition reaches display 88. Thereafter, the next time the CHNG DISP button 90-4 is pressed, display 84 will again become brilliant.

In the event that an erroneous, incorrect entry is displayed or for example is entered into the brilliant display, the entry may be cleared by pressing the C/E (clear entry) button 90-5.

The program for performing the inspection operation is comprised of a main program and a subroutine. The main program steps the XY table 12 beneath stereo-zoom microscopes 20 and 22 to each hybrid position to be inspected and more specifically steps XY table 12 to place the hole in the upper right-hand corner of each hybrid carrier 70 so that it is in alignment with the cross-hair of microscope 22. In this HOME position, the system then advances to the subroutine with steps the XY table 12 to place each of the target sites of the selected hybrid position to be inspected within the field of view of microscope 22. When all of the target sites have been inspected, the system then advances from the subroutine back to the main program which then steps to the next hybrid carrier position to be inspected, whereupon the system 10 again advances to the subroutine. The same subroutine is utilized throughout the inspection of all twelve hybrids since the hybrids under inspection are all of the same type and require inspection of the same target sites.

During execution of the main program, it is necessary to move XY table 12 so that a preselected point on each carrier 70 on the right-hand portion 59$b$ of tooling table 59 is brought into position and alignment with the cross-hairs of microscope 22. Thus, HOME button 96-9 is pressed, switch 92 is moved to the LOAD position, CHNG DISP button 90-4 is pressed until the M display 88 is brilliant and the appropriate decimal digit keys of keyboard array 90 are pressed to indicate start of the program, as will be more fully described. After checking the display 88 to be assured of its accuracy, the STORE button 90-6 is pressed to store the contents of display 88 and advance the sequence window 82 to display the decimal number "001".

The key switch 92 is then reset to the RUN position and the "jog" buttons 96-4 through 96-7 (or 42-5 through 42-8) are utilized to move XY table 12 so that first reference point is moved into alignment with the cross-hair of microscope 22. Preferably, the upper right-hand-most hole 72$c$-1$a$ in the carrier 70 is employed as the reference point. Microscope 22 is adjusted to bring the bottom of hole 72$c$-1$a$ into sharp focus and the XY Table 12 is jogged to bring the cross-hairs of the microscope 22 into alignment with the center of the hole.

Key switch 92 is then moved to the LOAD position, CHNG DISP button 90-4 is operated to advance the brilliant condition to display 88 and the digit keys "1" and "6" of keyboard array 90 are pressed to enter the decimal number "16" into display 88. Code "6" is a stop code while the code "1" causes the system 10 to jump to subroutine "1" which is the subroutine for inspecting all of the sites of the hybrid.

The STORE button 90-6 is pressed to store what is presently being displayed in M display 88. The above steps are then repeated until all reference points for the main program have been completed. Thereafter, the program is terminated and code "02" appears in M display 88. Code "02" is stored in memory by pressing STORE button 90-6.

To create the subroutine program, the same technique is followed except that the SUB RTN (subroutine) button 90-1 and the "+" button 90-2 are pressed, the main program is advanced to sequence 001, key switch 92 is operated to the LOAD position and the SUB RTN button 90-1 and the digit key "1" of array 90 are pressed to enter the code "−10" in display 88. The minus sign (−) signifies that a subroutine is being loaded.

If the data in display 88 is correct, STORE button 96-6 is pressed and the switch 92 is switched to the run position and the "jog" buttons 96-4 through 96-7 are operated to moved XY table 12 to the first inspection point at which time data in the display 84 (or 86) may be loaded into memory. However before doing so, the M functions are entered into display 88 and include one of the following: "6" for automatic stops; "7" for a dwell time of three (3) seconds; "8" for a dwell time of six (6) seconds; "9" for a return to the home position; "2" end of subroutine; and "0" for initiating recycling of the subroutine.

Programming an automatic stop into the first sequence of each portion of the subroutine, as was mentioned hereinabove, allows the operator time to adjust microscope 22 to the recommended magnifications and to refocus as and when needed and to switch cameras 24, 26 into or out of the circuit.

In case a longer dwell time is needed at any given reference point, this is accomplished by repeating any given sequence two or more times which, in turn, is accomplished by entering the data two or more times as successive program steps.

When the last step of the subroutine has been stored, the code −(1)2 is entered into the M display 88 and stored in order to provide an indication of the end of the subroutine.

After the program is completed, it may be examined when switch 92 is in the LOAD position by pressing ZERO SEQ button 90-7 which sequentially displays each program step. Changes may be made at this time in the M function by keying in the desired change and storing it in memory.

Programs created in the above manner may be loaded into a magnetic tape cassette (not shown) by pressing HOME button 96-9 (see FIG. 2), opening cover 94 of the tape unit 114 and inserting a blank tape cassette. Switch key 92 is then moved to the LOAD position and SUB RTN button 90-1 and "−" button 90-9 are pressed. The "000" display in the sequence display window 82 then disappears, during which time the entire contents of system memory is loaded into the tape of the tape cassette. After loading, the tape makes a second pass through the reader and compares the data in the cassette with the data in memory to verify that the data in the written tape agrees with the contents of the memory. After the recording and verification steps have been completed, the SEQUENCE display 82 generates a "000" display indicating that the program has been successfully transferred to the magnetic tape cassette.

The main program and the subroutine may be added to or modified through the use of the LOAD and RUN keyboards 90 and 96 as were described hereinabove.

The system 10 of FIG. 1 utilizes a microscope 20 and T.V. camera 24 for observing the known good hybrid. As an alternative embodiment, each target site of the known good hybrid may be recorded on a video tape or video disk or on a strip of photographic film.

In the embodiment employing a video tape or video disk, the aforementioned subroutine, in addition to moving the XY table 12 to position the proper target site of the hybrid under inspection beneath microscope 22, provides control signals through interface 134 or 148 (See FIG. 5) to control video tape playback device 138 or video disk playback device 150 to be advanced to the section of the video tape or video disk so that its read head (not shown) conveys the proper video signals to video display 34, enabling side-by-side comparison of the same target sites on both the known good hybrid and the hybrid under inspection.

In the embodiment where the target sites of the known good hybrid are recorded on a strip of photographic film, the microprocessor 102 controls projector interface circuit 154 to operator projector 156 to advance the film strip so that the correct target site is projected. T.V. camera 158 which is arranged within the optical circuit of the projector 156, converts the optical display into a video signal for display by video display device 34. The stereo-zoom microscope 20 is preferably retained in the system in order to permit observation of the known good hybrid during microscopic inspection of target sites to permit the operator to view the target sites for both the known good hybrid and the hybrid under inspection in order to confirm the accuracy of the operators inspection.

As was mentioned hereinabove, the sequence steps of the subroutine are utilized to insure inspection of every target site. In order to reduce the number of program steps to a practical minimum, adjustments may be made in the microscope magnification employed. Since an increase in magnification reduces the field of view, and vice versa, plural regions to be inspected may be incorporated into a common program step by appropriate reduction of the magnification setting of the microscope 22 thereby reducing the total number of target sites examined while at the same time being assured that every hybrid region to be examined is, in fact, included in the program.

A control system, which includes microprocessor 102 and which is suitable for use in the present system 10 is manufactured by Automation Unlimited Inc. and is identified as Model No. C-52. The video display 34 may, for example, be a Model EVM 1410 video monitor V2705P Inserter Splitter manufactured by ELECTROHOME Ltd. of Ontario, Canada, and a model SCA-V270 Inserter/Splitter modified by Sigma Communications (manufactured by Vicon Industries, Plainview, N.Y.). The stereo-zoom microscopes 20, 22 used in system 10 are produced by Bausch and Lomb. The TV cameras are Model HV-62SU CCTV cameras manufactured by Hitachi-Denshi, Ltd. of Japan. The XY table 12 may be any conventional type capable of advancing by increments of the order of 0.001 inch, as was described hereinabove, and may, for example, be of the type described in U.S. Pat. Nos. 3,881,362 and 3,703,834, although any other suitable XY table may be employed. The printer is a DIGITEC Series 6400 printer. It should be understood that other equipment having characteristic similar to those set forth herinabove may be substituted if desired.

A latitude of modification, change, and substitution is intended in the foregoing disclosure and, in some instances, some features of the invention will be employed without a corresponding use of other features. Accordingly, it is appropriate that the appended claims be construed broadly and in a manner consistent with the spirit and scope of the invention herein.

What is claimed is:

1. Inspection apparatus for inspecting a plurality of target sites on miniaturized devices comprising:

XY table means having a mounting surface provided with
plural mounting means;
positioning means coupled to said XY table means for moving said mounting surface in mutually perpendicular directions;
optical viewing means positioned above said mounting surface for enabling an operator to view the site on the surface of said table means beneath said optical viewing means;
plural holding means each being removably receivable on one of said mounting means for accurately positioning at least one of said miniaturized devices upon said mounting surface;
microprocessor means coupled to said positioning means for positioning selected portions of said miniaturized devices in a sequential fashion beneath said optical viewing means in a predetermined sequence in accordance with a program stored in said microprocessor means; and
video display means coupled to said optical viewing for displaying the site presented by said optical viewing means enabling an operator to view the site under inspection through either the optical viewing means or the video display means.

2. The inspection apparatus of claim 1 further comprising means for selectively connecting said video display means to said optical viewing means.

3. The inspection apparatus of claim 1 further comprising video display means including video playback means adapted to selectively display stored video information in the form of target sites of a known good miniaturized device corresponding to each of the target sites of the miniaturized device under inspection under control of said microprocessor means whereby the the video display means displays corresponding target sites of the miniaturized device being inspected and the stored video image of the known good miniaturized device.

4. The inspection apparatus of claim 1 wherein said video display means comprises a video display device;
video disk playback means coupled to said video display device for displaying the target area of a known good miniaturized device previously recorded on a video disk under control of said microprocessor means for comparing the target site of the known good miniaturized device with the target site of the miniaturized device under inspection.

5. The inspection apparatus of claim 1 further comprising printer means having a keyboard for entering data representing observations at selected ones of the target sites.

6. The inspection apparatus of claim 5 wherein said microprocessor includes means responsive to operation of said printer means keyboard for automatically printing data representing the target site presently in view at the time the observation data is entered into said printer means.

7. The inspection apparatus of claim 1 wherein said microprocessor means further comprises means for temporarily halting the program in process at predetermined site locations;
manually operable jogging means for displacing said XY table means from its present position to permit observation beyond the field of view of the present target site; and
restart means for causing said microprocessor means to resume said program.

8. The inspection apparatus of claim 7 wherein said restart means further comprises manually operable means for enabling said microprocessor means to reinitiate the program, said microprocessor means including means controlling said positioning means to move said XY table means to place the next target site called for in the program beneath the optical viewing means regardless of the displacement imposed on the XY table means by said jogging means.

9. The inspection apparatus of claim 1 further comprising display means for visually displaying the displacement distance between a predetermined arbitrary home position on the surface of said XY table means and the present position of said mounting surface.

10. The inspection apparatus of claim 9 wherein said display means comprises first and second digital displays for displaying said displacement distance respectively measured along an X axis and a Y axis from said arbitrary home position.

11. The inspection apparatus of claim 10 wherein said display means further comprises a third digital display for displaying the step in the program sequence last performed by said microprocessor means.

12. The inspection apparatus of claim 1 wherein said microprocessor means further comprising means for adjusting the dwell time between the completion of the last movement of the XY table means and the next movement of the XY table means to provide the operator with sufficient time to view the target site presently in view.

13. The inspection apparatus of claim 1 further comprising:
said holding means supporting each of said miniaturized devices in a predetermined location; and
said supporting surface mounting means comprising a plurality of sets of locating means each for positively receiving and locating one of said carrier means on said supporting surface.

14. Inspection apparatus for inspecting a plurality of target sites on miniaturized devices comprising:
XY table means having a mounting surface;
positioning means coupled to said XY table means for moving said mounting surface in mutually perpendicular directions;
optical viewing means positioned above said mounting surface for enabling an operator to view the site on the surface of said table means beneath said optical viewing means;
means for positioning at least one of said miniaturized devices upon said mounting surface;
microprocessor means coupled to said positioning means for positioning selected portions of said miniaturized devices in a sequential fashion beneath said optical viewing means in a predetermined sequence in accordance with a program stored in said microprocessor means;
video display means coupled to said optical viewing for displaying the site presented by said optical viewing means enabling an operator to view the site under inspection through either the optical viewing means or the video display means;
carrier means for supporting each of said miniatured devices in a predetermined location;
said supporting surface having a plurality of sets of locating means each for positively receiving and locating one of said carrier means on said supporting surface;

a known good miniaturized device being arranged on a second one of said carrier means; and each of said aforementioned carrier means being arranged beneath an associated one of said first and second optical display means.

15. The inspection apparatus of claim 14 wherein said optical display means comprises first and second stereo-zoom microscopes.

16. The inspection apparatus of claim 14 wherein said miniaturized devices are electronic solid-state hybrid circuits having a plurality of connecting pins arranged in first and second arrays along opposing sides of said hybrid;

each of said carrier means comprising a solid member having a plurality of rows of openings arranged to receive said connecting pins.

17. The inspection apparatus of claim 16, wherein each of said carrier means is provided with at least a pair of mounting pins; and said locating means comprising a pair of openings for receiving the mounting pins of said carrier means to precisely locate said carrier means upon said supporting surface.

18. Inspection apparatus for inspecting a plurality of target sites on miniaturized devices comprising:

XY table means having a mounting surface;

positioning means coupled to said XY table means for moving said mounting surface in mutually perpendicular directions;

optical viewing means positioned above said mounting surface for enabling an operator to view the site on the surface of said table means beneath said optical viewing means;

first holding means each for positioning at least one of said miniaturized devices upon said surface;

microprocessor means operating said positioning means for positioning selected portions of said miniaturized device beneath said optical viewing means in a predetermined sequence in accordance with a program stored in said microprocessor means;

video display means for displaying the site presented by said optical viewing means, and said video display means further comprising means for simultaneously displaying corresponding sites of a known good miniaturized device and of the miniaturized device being inspected to provide for side-by-side comparison.

19. The inspection apparatus of claim 18 wherein said video display means comprises split screen display means.

20. The inspection apparatus of claim 19 wherein said video display means further comprises means for selectively increasing the size and/or magnification of the sites displayed by said split screen display means.

21. The inspection apparatus of claim 18 further comprising means for selectively disabling either one of the target sites being displayed on said split screen display means.

22. The inspection apparatus of claim 21 wherein said video display means further comprises means for enlarging the display to enable the selected target site to occupy the entire screen of the video display means.

23. Inspection apparatus for inspecting a plurality of target sites on miniaturized devices comprising:

XY table means having a mounting surface;

positioning means coupled to said XY table means for moving said mounting surface in mutually perpendicular directions;

first and second optical viewing means positioned at spaced intervals above said mounting surface for enabling an operator to view spaced sites on the surface of said table means beneath said first and second optical viewing means;

first holding means for positioning at least one miniaturized device to be examined on said surface;

second holding means for positioning a known good miniaturized device at a second position upon said surface;

microprocessor means coupled to said positioning means for positioning selected portions of the aforementioned miniaturized devices beneath respective ones of said first and second optical viewing means in a predetermined sequence, in accordance with a program stored in said microprocessor means; and video display means coupled to said first and second optical viewing means for simultaneously displaying the sites presented by said first and second optical viewing means, enabling an operator to view the sites under inspection through either the first and second optical viewing means or the video display means.

24. The inspection apparatus of claim 23 wherein:

said second holding means for mounting a known good miniaturized device is positioned beneath said second optical viewing means so that the target sites viewable by both of said optical viewing means are the same, regardless of the position to which said XY table means is moved;

said first and second optical viewing means each conveying an image to an associated one of said first and second television cameras; and said video display means including means for generating a visual display coupled to said first and second television cameras for simultaneously displaying the images conveyed to said visual display means.

25. The inspection apparatus of claim 24 further comprising first and second T.V. cameras coupled between said first and second optical viewing means and said video display means.

26. The inspection apparatus of claim 23 further comprising viewing selection means coupled to said video display means for selectively displaying the sites viewed by said first and second optical viewing means on first and second display portions of said video display means.

27. The inspection apparatus of claim 26 wherein said viewing selection means comprises means for selectively altering the size of each object displayed in said viewing portions.

28. The inspection apparatus of claim 27 wherein said viewing selection means further comprises means for selectively displaying only one of the sites viewed by the first and second optical viewing means.

29. Inspection apparatus for inspecting a plurality of target sites on miniaturized devices comprising:

XY table means having a mounting surface;

positioning means coupled to said XY table means for moving said mounting surface in mutually perpendicular directions;

optical viewing means positioned above said mounting surface for enabling an operator to view the site on the surface of said table means beneath said optical viewing means;

means for positioning at least one of said miniaturized devices upon said mounting surface;

microprocessor means coupled to said positioning means for positioning selected portions of said miniaturized devices in a sequential fashion beneath said optical viewing means in a predetermined sequence in accordance with a program stored in said microprocessor means;

video display means coupled to said optical viewing for displaying the site presented by said optical viewing means enabling an operator to view the site under inspection through either the optical viewing means or the video display means, said video display means comprising a video display device;

projector means responsive to said microprocessor means for displaying a target site of a known good miniaturized device previously recorded upon a film strip arranged in said projector; and means for converting the output of the projector means to electrical signals for causing said video display device to display the selected target site of the known good miniaturized device.

30. A method for inspecting a miniaturized device by examining a large number of target sites thereon through the use of inspection apparatus including: a motor driven XY table means; first and second optical viewing means; video display means; printer means; and a keyboard for entering data, said method comprising the steps of:

(a) placing the miniaturized device to be inspected at a first location on said table means and placing a known good miniaturized device at a second location on said XY table means;

(b) advancing said table means to simultaneously position a predetermined target site of both of said miniaturized devices beneath said first and second optical viewing means to enable the operator to view and compare said target site through the use of either said optical viewing means or said visual display means, which includes a split screen for displaying corresponding sites of said miniaturized devices in side-by-side fashion;

(c) providing a dwell interval to provide sufficient time for viewing each of the target sites;

(d) moving said table to the next target site at the end of said dwell interval; and (e) operating the printer means to enter a code representing the target site presently beneath the optical viewing means whenever the keyboard of the printer means is operated.

* * * * *

UNITED STATES PATENT AND TRADEMARK OFFICE
CERTIFICATE OF CORRECTION

PATENT NO. :   4,389,669
DATED      :   June 21, 1983
INVENTOR(S) :  Epstein, et al.

It is certified that error appears in the above—identified patent and that said Letters Patent is hereby corrected as shown below:

Column 6:

Line 21, change "vary" to --very--.

Column 9:

Line 40, change "1124" to --124--;

Line 44, change "(not" to --(note--.

Column 11:

Line 18, change "buttom" to --button--.

Signed and Sealed this

Twentieth  Day of  December 1983

[SEAL]

Attest:

GERALD J. MOSSINGHOFF

Attesting Officer            Commissioner of Patents and Trademarks